United States Patent [19]
Karasawa

[11] Patent Number: 5,738,632
[45] Date of Patent: Apr. 14, 1998

[54] DEVICE FOR USE IN COMBINATION WITH A MAGNETIC RESONANCE IMAGING APPARATUS

[75] Inventor: Masaru Karasawa, Hachioji, Japan

[73] Assignee: Olympus Optical Co., Ltd., Tokyo, Japan

[21] Appl. No.: 405,203

[22] Filed: Mar. 16, 1995

[30] Foreign Application Priority Data

| Mar. 18, 1994 | [JP] | Japan | 6-049097 |
| Mar. 9, 1995 | [JP] | Japan | 7-049501 |

[51] Int. Cl.⁶ .................................................. A61B 5/055
[52] U.S. Cl. ........................ 600/410; 600/435; 324/318
[58] Field of Search ..................... 128/653.2, 653.5, 128/658; 600/138, 139, 101, 109, 160, 407, 410, 435; 324/318, 322, 309

[56] References Cited

U.S. PATENT DOCUMENTS

| 4,361,139 | 11/1982 | Takagi | 600/138 |
| 4,827,931 | 5/1989 | Longmore | 128/653.2 |
| 4,932,411 | 6/1990 | Fritschy et al. | 128/653.2 |
| 4,989,608 | 2/1991 | Ratner | |
| 5,170,789 | 12/1992 | Narayan et al. | |
| 5,188,111 | 2/1993 | Yates et al. | |
| 5,273,041 | 12/1993 | Richards et al. | 128/653.2 |
| 5,432,450 | 7/1995 | Rubinson | 324/318 |
| 5,476,090 | 12/1995 | Kishi | 600/138 |

FOREIGN PATENT DOCUMENTS

| 0165742 | 12/1985 | European Pat. Off. |
| 0576016 A1 | 12/1993 | European Pat. Off. |
| 6-165768 | 6/1994 | Japan |
| 6-165769 | 6/1994 | Japan |
| 6-269421 | 9/1994 | Japan |
| WO 86/010932 | 2/1986 | WIPO |

OTHER PUBLICATIONS

Patent Abstracts of Japan, vol. 15, No. 456 (C–886) Nov. 20, 1991 & JP-A-03 195 563 (Nipon Zeon Co., Ltd.) Aug. 27, 1991.

*Primary Examiner*—Brian L. Casler
*Attorney, Agent, or Firm*—Frishauf, Holtz, Goodman, Langer & Chick

[57] ABSTRACT

A device for use in combination with a magnetic resonance imaging apparatus which generates a static magnetic field and detects magnetic resonances in a living body is placed in the static magnetic field, includes a distal end portion and another portion having an end connected to the distal end portion. The distal end portion has a magnetic permeability of such a value that diagnosis and treatment are not influenced by magnetic resonance image distortions due to a disturbance in a uniformity of the static magnetic field generated by the apparatus. The device includes other portions which have a magnetic permeability which is higher than that of the distal end portion and have a value so that the other portions are prevented from being attracted to the static magnetic field. The device does not adversely influence magnetic resonance images since the device is not attracted to a magnet of the magnetic resonance imaging apparatus, thereby increasing an accuracy in diagnosis and treatment.

8 Claims, 11 Drawing Sheets

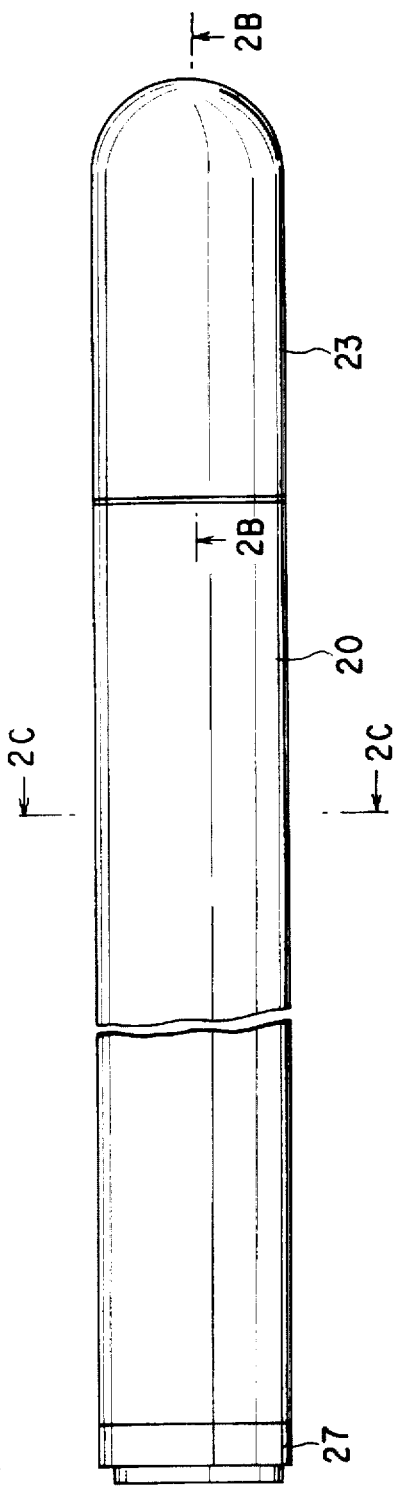
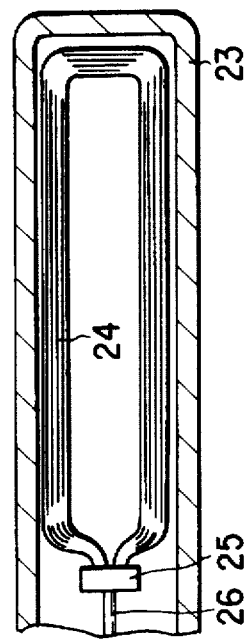
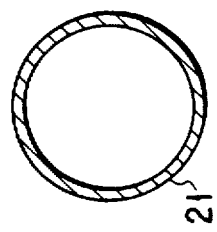
FIG. 2A
FIG. 2B
FIG. 2C

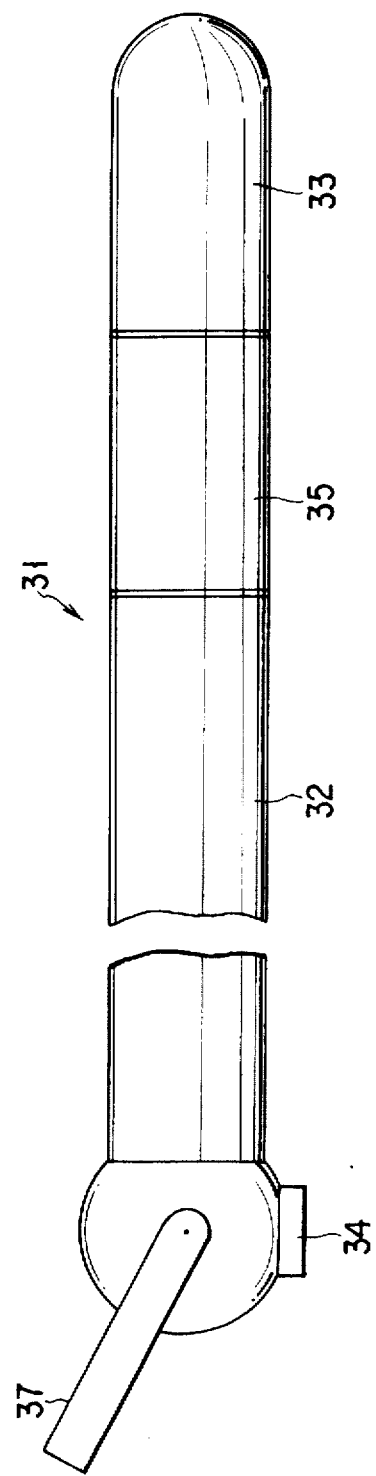

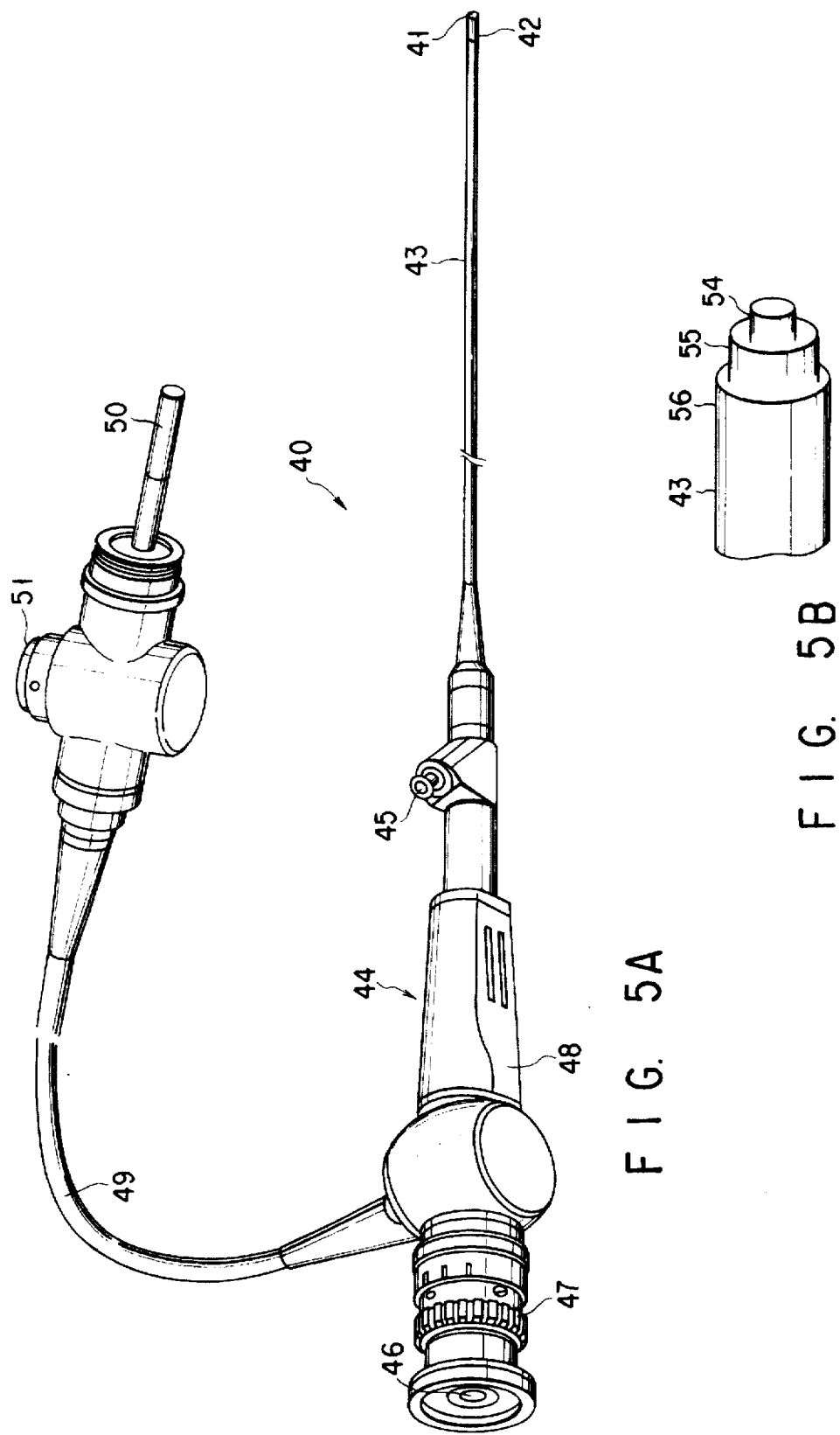
F I G. 5A
F I G. 5B

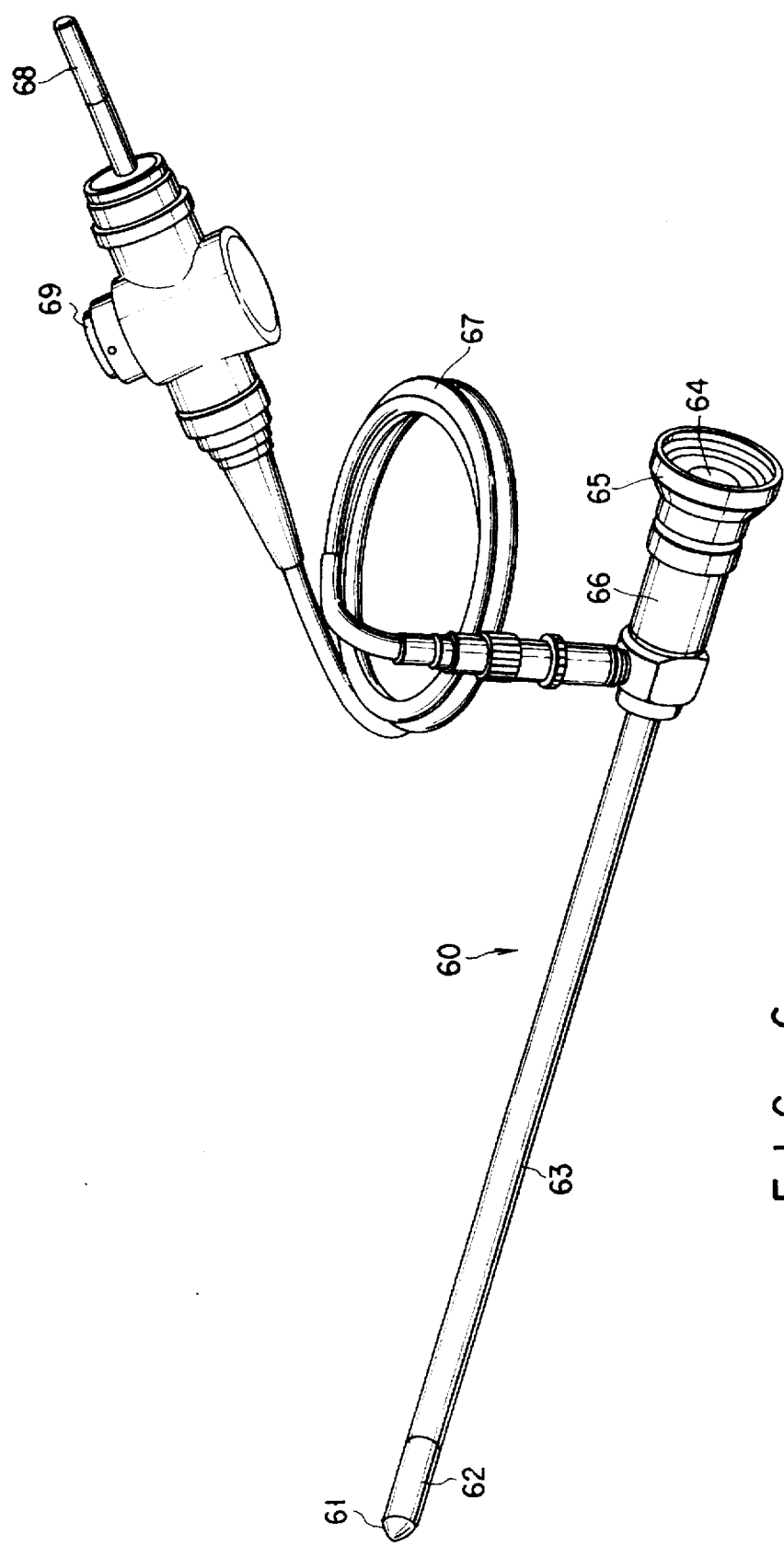

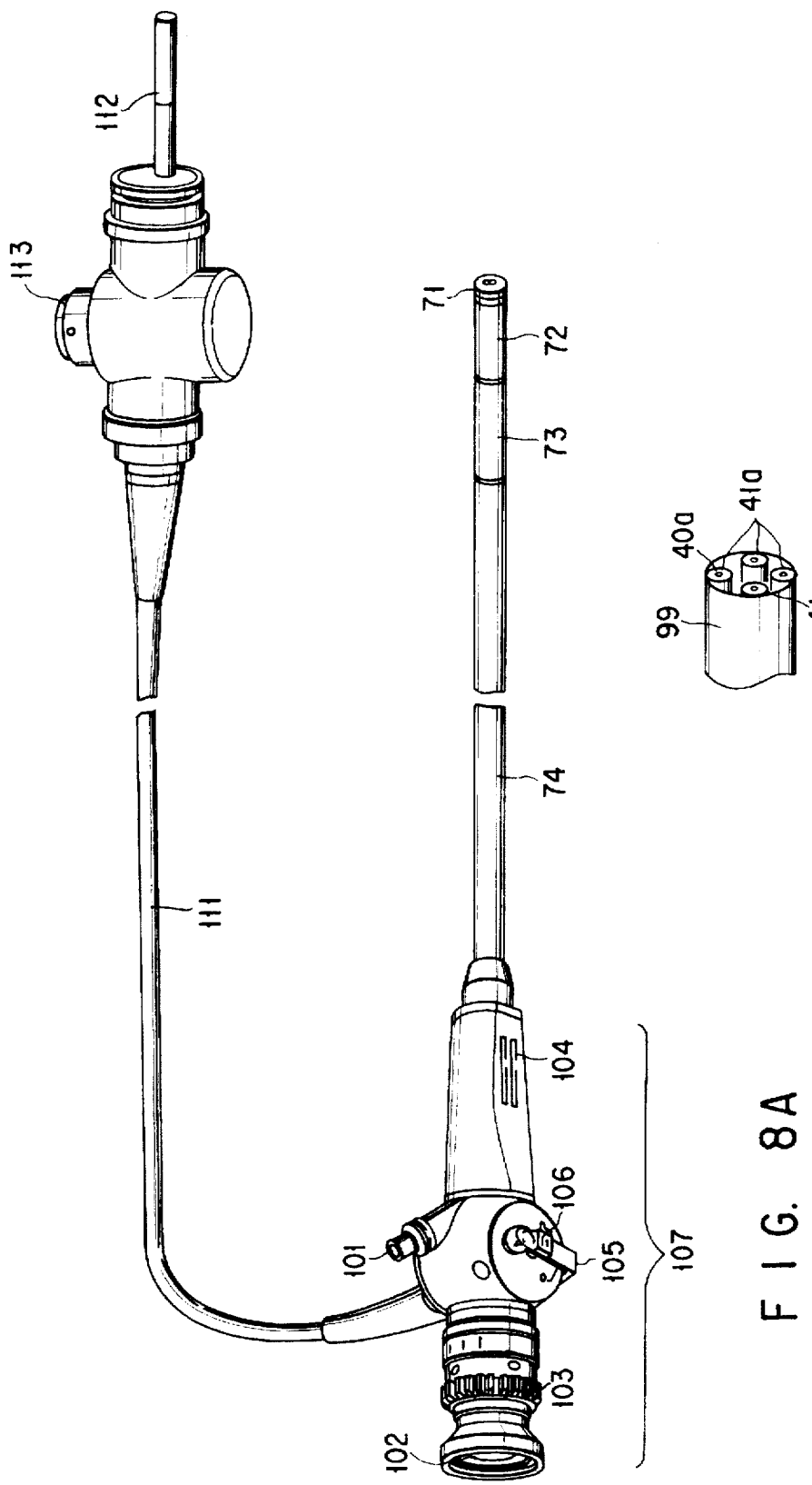

DEVICE FOR USE IN COMBINATION WITH A MAGNETIC RESONANCE IMAGING APPARATUS

BACKGROUND OF THE INVENTION

1. Field of the Invention

The present invention relates to a device for use in combination with a magnetic resonance imaging apparatus, which can be inserted into a body cavity and which detects a magnetic resonance signal in the cavity and supplies the signal to the imaging apparatus so that the apparatus may form a magnetic resonance image for diagnostic use.

2. Description of the Related Art

A magnetic resonance imaging apparatus for receiving a magnetic resonance signal generated in a body cavity is disclosed in Jpn. Pat. Appln. KOKAI Publication No. 6-269421. This apparatus is used in combination of a device which is similar in structure to an ordinary endoscope.

The device comprises a distal end section, an insertion section, an operating section and a universal cord. The distal end section comprises a high-frequency coil, a container, a bending portion and an optical system. The high-frequency coil detects a magnetic resonance signal. The container contains the coil. The optical system has an observation unit and an illumination unit. The distal end section has holes through which forceps can be inserted into and removed from a body cavity and through which liquids can be applied into and removed from the body cavity. The insertion section and the universal cord are covered with an outer sheath which is a flexible tube. The operation section has means for controlling the bending of the bending portion and air supply and water supply through the holes of the distal end portion. The operation section has holes through which forces and other medical instruments can be guided into a body cavity.

When used in combination with the device, the magnetic resonance imaging apparatus can provide an endoscope image and a magnetic resonance image, which are examined to make diagnosis.

The device disclosed in Publication No. 6-269421 is disadvantageous, however, in that its components used in an intense static magnetic field do not have appropriate magnetic permeabilities or magnetic susceptibilities. If the components constituting the flexible tube are made of material having high magnetic permeabilities, they will be attracted to the magnet of the magnetic resonance imaging apparatus, inevitably resulting in an inconvenience in use. Further, these components will impair the uniformity of the static magnetic field generated by the magnet, ultimately deteriorating the MR image.

SUMMARY OF THE INVENTION

The object of the present invention is to provide a device for use in combination with a magnetic resonance imaging apparatus, which does not adversely influence the MR image formed by the apparatus, which is not attracted to the magnet of the apparatus, thereby ensuring high safety for operators and patients and having high operability, and which can reliably detect magnetic resonance signals from living tissues.

According to a first aspect of the invention, there is provided a device which is designed for use in combination with a magnetic resonance imaging apparatus and which has a distal end section which can be inserted into a body cavity. The device comprises a first portion and a second portion. The first portion has at least one of a magnetic permeability and a magnetic susceptibility which has such a value that diagnosis and treatment are not influenced by a magnetic resonance image distorts caused by disturbance in the uniformity of the static magnetic field generated by the apparatus. The second portion has at least one of a magnetic permeability and a magnetic susceptibility which is higher than that of the distal end section and is of such a value that the second portion is not attracted to the static magnetic field.

According to a second aspect of the invention, there is provided a device which is designed for use in combination with a magnetic resonance imaging apparatus and which has a distal end section which can be inserted into a body cavity. The device comprises a first portion, a second portion and a third portion. The first portion can enter a region to be imaged by the apparatus and has at least one of a magnetic permeability and a magnetic susceptibility which has such a value that diagnosis and treatment remain not influenced by a magnetic resonance image distorted due to disturbance in the uniformity of the static magnetic field generated by apparatus. The second portion cannot enter a body cavity and has at least one of a magnetic permeability and a magnetic susceptibility which is higher than that of the distal end section and has such a value that the second portion is not attracted by the static magnetic field. The third portion cannot enter the region to be imaged, can enter the body cavity, and has at least one of a magnetic permeability and a magnetic susceptibility which is higher than that of the first portion and lower than that has the second portion and of such a value that disturbances in the uniformity of the static magnetic field are small.

Since the device does not disturb the uniformity of the static magnetic field while a subject is being examined or is receiving treatment, the parts of the subject, being examined or receiving treatment can be observed in the form of MR images which are not distorted. Further, non-attraction to the static magnetic field ensures high safety for an operator and the subject and has high operability. Moreover, since it is only the distal end section that needs to have a magnetic permeability which is too small to deteriorate MR images, the device is simple in structure and can be manufactured at low cost.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A, 2B and 2C are views schematically showing the structure of a device according to fourth, fifth and sixth embodiments of the present invention;

FIG. 4 is a view schematically showing the structure of a device according to tenth to twelfth embodiments of the present invention;

FIGS. 5A and 5B are views schematically showing the structure of a device according to thirteenth to fifteenth embodiments of the present invention;

FIG. 6 is a view schematically showing the structure of a device according to sixteenth to eighteenth embodiments of the present invention;

FIGS. 8A and 8B are views schematically showing the structure of a device according to twenty-second, twenty-third, and twenty-fourth embodiments of the present invention;

DETAILED DESCRIPTION

First Embodiment

Figure 1A:
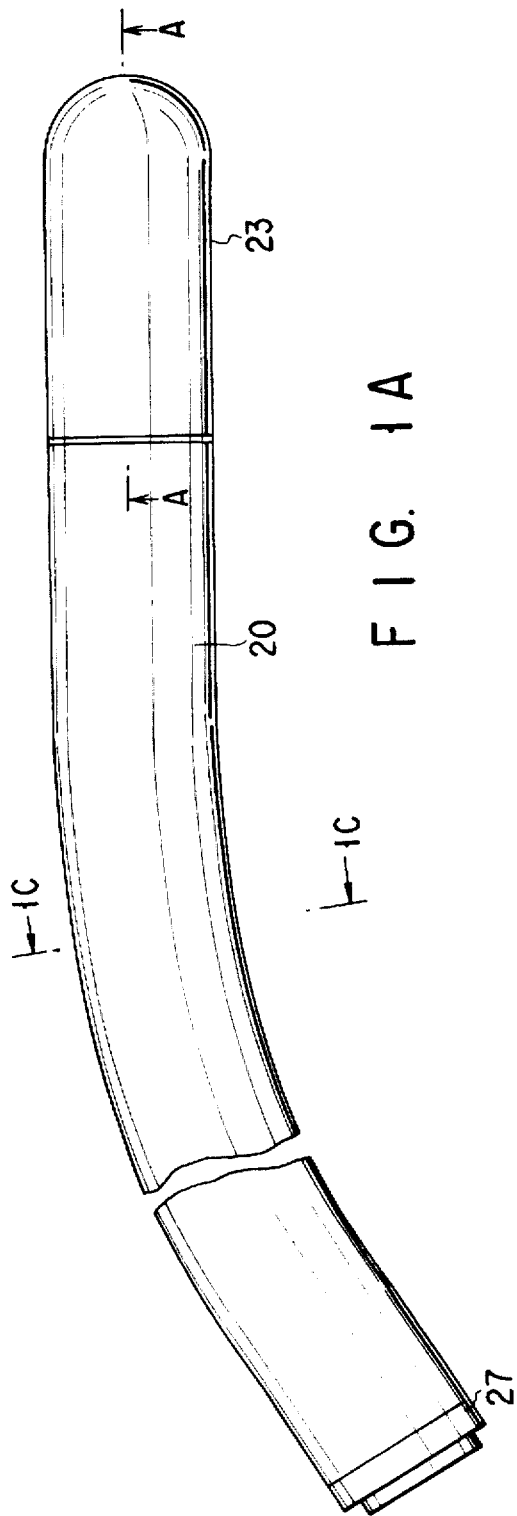
FIGS. 1A, 1B and 1C are views schematically showing the structure of a device according to first, second and third embodiments of the present invention.
Figure 1B:
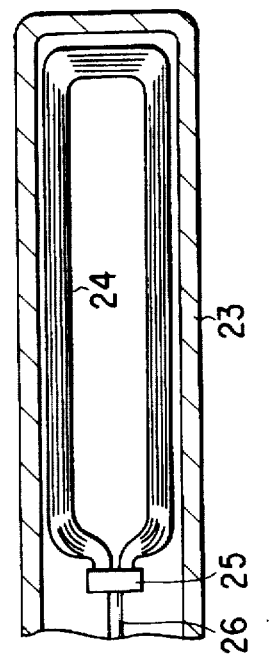
Figure 1C:
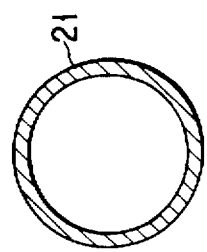

FIGS. 1A, 1B and 1C schematically show the structure of a device for a magnetic resonance imaging apparatus according to the first embodiment of the present invention. In these figures, FIG. 1A shows the entire device, FIG. 1B is a cross-section cut along a line A—A of FIG. 1A, and FIG. 1C is a cross section cut along a line C—C of FIG. 1A.

In this first embodiment, an insertion portion 20 of the device can be inserted into body cavities of a patient and is formed of at least one layer of a flexible tube 21. A distal end portion 23 is provided at the top end of the insertion portion 20. The distal end portion 23 comprises of a cylindrical container member made of a material having a low dielectric constant, and particularly, the top end of the portion 23 is enclosed to be round. As shown in FIG. 1B, a magnetic resonance signal receiver coil (portion) 24 having a loop-like shape as a receiver coil means for receiving a magnetic resonance signal and a rectifier circuit 25 are included in the distal end portion 23. Further, a transmit means 26 for transmitting a magnetic resonance signal received by the magnetic resonance signal receiver coil 24 is provided in the tube 21 of the insertion portion 20. The transmit means 26 transmits the magnetic resonance signal to the magnetic resonance signal output portion 27.

The magnetic resonance signal output portion 27 is provided at a bottom end of the insertion portion 20. The magnetic resonance signal output portion 27 has a function as a connector to the magnetic resonance imaging apparatus (MRI) coupled with the device, so that the output portion 27 outputs the magnetic resonance signal received by the distal end portion 23 to the magnetic resonance imaging apparatus.

The material of a first portion which forms the distal end portion 23 in the device body has a magnetic permeability or magnetic susceptibility which is lower than that of the tube 21 of the insertion portion forming a second portion as a remaining other portion of the device body and that of a material forming the magnetic resonance signal output portion 27 and is within such a range that does not disturb the uniformity of a static magnetic field generated by the magnetic resonance imaging apparatus. Specifically, the first portion forming the distal end portion 23 is made of a material which has such a magnetic permeability or magnetic susceptibility that causes only a negligible disturbance in uniformity of the static magnetic field so that a distortion of a magnetic resonance cross-section image resulting from the disturbance is considered as not influencing on a diagnosis or a treatment.

As a typical example which provides a distinguishable magnetic permeability or magnetic susceptibility as stated above, there may be a distal end portion 23 made of an material having a extremely small magnetic susceptibility such as a resin, a non-magnetic metal, or the like, when a low magnetic permeability metal or a low magnetic susceptibility metal having a feeble magnetism is included in materials forming the insertion portion 20 and magnetic resonance signal output portion 27.

In addition, the shape of the distal end portion is not limited to that specified above, as long as the requirements also specified above are satisfied. The shape of the magnetic resonance signal receiver coil 24 is not limited to a loop-like shape. The material of the magnetic resonance signal receiver coil 24 is not limited to gold, silver, copper, and aluminum, as long as it is a low magnetic permeability metal which is electrically conductive. Further, the shape and lay-out of components inside the distal end portion 23 are not limited to the structure as specified above.

As has been explained above, according to the first embodiment of the present invention, an insertion portion 20 of the device is inserted into a body and the distal end portion 23 is precisely positioned at a target portion. After the insertion, a magnetic resonance signal received by a magnetic resonance signal receiver coil 24 included in the distal end portion 23 is transmitted to a magnetic resonance imaging apparatus not shown through a transmit means 26 and a magnetic resonance signal output portion 27 connected thereto, and accordingly, an MR-image is obtained. An operator carries out a diagnosis on the basis of the MR-image.

Thus, in the structure of this embodiment, the insertion portion 20 can be easily inserted into body cavities, thereby incurring less burdens onto a patient's body, and the insertion portion 23 can be precisely positioned at a target portion.

Further, if the insertion portion of this device is inserted into a body, uniformity in the static magnetic field in the area whose MR-image is being picked up can be maintained so that distortions do not appear on the MR-image since the material forming the periphery of the magnetic resonance signal receiver coil 24 has an extremely small magnetic susceptibility in the vicinity of the coil 24. This means that magnetic resonance signals can be received directly from the body cavities, and that clear MR-images can be obtained without deterioration in image quality since the distal end portion 23 inserted into a body does not disturb the magnetic field.

If a structure of an endoscope is incorporated in this device, the device further has a structure as a soft scope so that observation using the endoscope function can simultaneously be carried out. The material of the structure of the endoscope must naturally be considered as having the same magnetic susceptibility as stated above.

Second Embodiment

This second embodiment has a structure of the same type as the first embodiment. In this embodiment, the material forming the distal end portion 23 provided at the top end of the flexible tube 21 constituting the insertion portion 20 of the device for a magnetic resonance imaging apparatus has a magnetic permeability lower than that of the material forming the insertion portion 20 and the magnetic resonance signal output portion. The distal end portion 23 can be inserted into a body and is a first portion which enters into at least the area to be picked up by the magnetic resonance imaging apparatus. The magnetic resonance signal output portion 27 is a second portion which cannot be inserted into the body.

Further, a portion forming the tube 21 constituting the insertion portion 20 is a third portion which does not enter into the area to be picked up by the magnetic resonance imaging apparatus but can be inserted into the body. The material of this third portion has a magnetic permeability lower than that of the material forming the magnetic resonance signal output portion 27 which cannot be inserted into the body. Specifically, the magnetic susceptibility of this third portion is a value between the magnetic susceptibility of the first portion and the magnetic susceptibility of the second portion, within such a range which causes only a small disturbance in the static magnetic field generated by the magnetic resonance imaging apparatus. As a typical example of this, there may be an insertion portion 20 made of titanium, titanium alloy, austenite-based stainless steel or the like which is slightly magnetized by means of some treatments or the like, and a distal end portion made of resins, copper, copper alloy, aluminum alloy, or titanium or titanium alloy which has a negligibly small magnetic susceptibility, when low magnetic permeability metal or low magnetic susceptibility metal having a feeble magnetism is included in the materials forming the magnetic resonance signal output portion 27 corresponding to a portion having a shape and arranged at a position which cannot be inserted into a body.

The distal end portion may be made of copper (magnetic susceptibility $\chi=-0.0086\times10^6$), copper alloy having similar magnetic susceptibility, resin, titanium, titanium alloy or aluminum ($\chi=0.61\times10^6$). The insertion portion which can be inserted into a body cavity but is not moved to an imaging region may be made of any one of these materials and worked upon to be magnetized. The portion which can be inserted into a body cavity may be made of SUS304 which is austenite-based stainless steel (magnetic permeability $\mu=1.0037$) or SUS310 which is also austenite-based stainless steel (annealed, magnetic permeability $\mu=1.0018$). The insertion portion can be made of either SUS304 or SUS310 under the nomination of the JIS.

The material specified above which have the magnetic susceptibilities and permeabilities mentioned are no more than a few examples. The distal end portion, the insertion portion, and the portion able to enter a body cavity can be made of other materials which exhibit magnetic susceptibilities and permeabilities different from those mentioned above.

In addition, the shapes of components are not limited to those specified above, as long as the requirements also specified above are satisfied. The shape of the magnetic resonance signal receiver coil 24 is not limited to a loop-like shape. The material of the magnetic resonance signal receiver coil 24 is not limited to copper, as long as it is a low magnetic permeability metal which is electrically conductive. Further, the insertion portion 20 uses a material which has the lowest magnetic permeability if necessary, as long as the material does not influence an MR-image.

The second embodiment having the above structure attains the same operation as the first embodiment. Therefore, according to the this embodiment, the same advantages as shown in the first embodiment can be obtained. Further, since not only the distal end portion 23 but also the insertion portion 20 are not attracted by a magnet of a magnetic resonance video device and the magnetism of the insertion portion 20 does not cause such influences which disturb the static magnetic field in the area whose MR-image is being picked up, distortions of the MR-image is eliminated and safety can be ensure for both of an operator and a patient.

Third Embodiment

This third embodiment has a structure of the same type as the first embodiment. In this embodiment, however, the material forming the distal end portion 23 of the device for a magnetic resonance imaging apparatus has a magnetic permeability lower than that of the material forming the insertion portion 20 and the magnetic resonance signal output portion. In addition, the material forming the insertion portion 20 has a magnetic permeability lower than that of the material forming the magnetic resonance signal output portion 27. Further, the material forming the magnetic resonance signal output portion 27 has a magnetic permeability equal to or lower than metallic materials forming a conventional endoscope operating portion.

Shapes are not limited to those specified above, as long as the requirements also specified above are satisfied. The shape of the magnetic resonance signal receiver coil 24 is not limited to a loop-like shape. The material of the magnetic resonance signal receiver coil 24 is not limited to copper, as long as it is a low magnetic permeability metal which is electrically conductive. Further, the insertion portion 20 uses a material which has the lowest magnetic permeability if necessary, as long as the material does not influences an MR-image.

The second embodiment having the above structure attains an advantage in that the magnetic resonance signal output portion 27 is not attracted by a magnet of a magnetic resonance video device so that safety can be ensured for both of an operator and a patient, in addition to the advantages as explained in the first and second embodiments.

Fourth Embodiment

FIGS. 2A, 2B and 2C schematically show the structure of a device for a magnetic resonance imaging apparatus according to the fourth embodiment of the present invention. In these figure, FIG. 2A shows the entire device, FIG. 2B is a cross-section cut along a line 2B—2B of FIG. 2A, and FIG. 2C is a cross section cut along a line 2C—2C of FIG. 2A.

In this fourth embodiment, an insertion portion 20 of the device has a structure basically common to the first embodiment. However, the tube 21 which can be inserted into body cavities and is formed of at least one layer is not flexible but is a rigid tube.

According to the fourth embodiment having the structure as stated above, since the tube 21 constituting the insertion portion 20 is hard, the insertion portion 20 is useful when it is inserted into a body, especially, into a ventricle, a pleural cavity, a joint, or a peritoneal cavity, and the distal end portion 23 can be precisely positioned at a target portion. Further, according to this embodiment, a tube can be easily inserted into a body, particularly into a ventricle, a pleural cavity, a joint, or a peritoneal cavity. The other operation and advantages are the same as those of the first embodiment described above.

If a structure of an endoscope is incorporated in this device, the device further has a structure as a rigid scope so that observation using the endoscope function can simultaneously be carried out. The material of the structure of the endoscope must naturally be considered as having the same magnetic susceptibility as stated above.

Fifth Embodiment

This second embodiment has a structure similar to the fourth embodiment, except that, the material forming the distal end portion 23 of this embodiment has a magnetic permeability lower than that of the material forming the insertion portion 20 and the magnetic resonance signal output portion 27.

Further, the material forming the insertion portion 20 has a magnetic permeability lower than that of the material forming the magnetic resonance signal output portion 27. As a typical example of this, there is an insertion portion 20 made of resins, copper, copper alloy, or aluminum alloy, when iron having a high purity is included in the material forming the magnetic resonance signal output portion 27.

In addition, the shapes are not limited to those specified above, as long as the requirements also specified above are satisfied. The shape of the magnetic resonance signal receiver coil 24 is not limited to a loop-like shape. The material of the signal receiver coil 24 is not limited to copper, as long as it is a low magnetic permeability metal which is electrically conductive.

The fifth embodiment having the above structure attains the same operation as the fourth embodiment. Therefore, according to this embodiment, the same advantages as shown in the first embodiment can be obtained. Further, according to this fifth embodiment, not only the distal end portion 23 but also the insertion portion 20 is not attracted by a magnet of a magnetic resonance video device, so that safety can be ensured for both of an operator and a patient.

Sixth Embodiment

This sixth embodiment has the same structure as the first embodiment, except as to the following respect. Specifically, the material forming the distal end portion 23 has a magnetic permeability lower than those of the materials forming the insertion portion 20 and the magnetic resonance signal output portion 27, and the material forming the insertion portion 20 has a magnetic permeability lower than that of the material forming the magnetic resonance signal output portion 27. Further, the material forming the magnetic resonance signal output portion 27 has a magnetic permeability equal to or lower than metallic materials forming a conventional endoscope operating portion.

The sixth embodiment having the above structure performs the same operation as that of the fourth embodiment described above. Further, according to the this embodiment, an advantage is obtained in that the magnetic resonance signal output portion 27 is not attracted by a magnet of a magnetic resonance imaging apparatus so that safety can be ensured for both of an operator and a patient, in addition to the advantages as explained in the fifth embodiment.

Seventh Embodiment

Figure 3A:
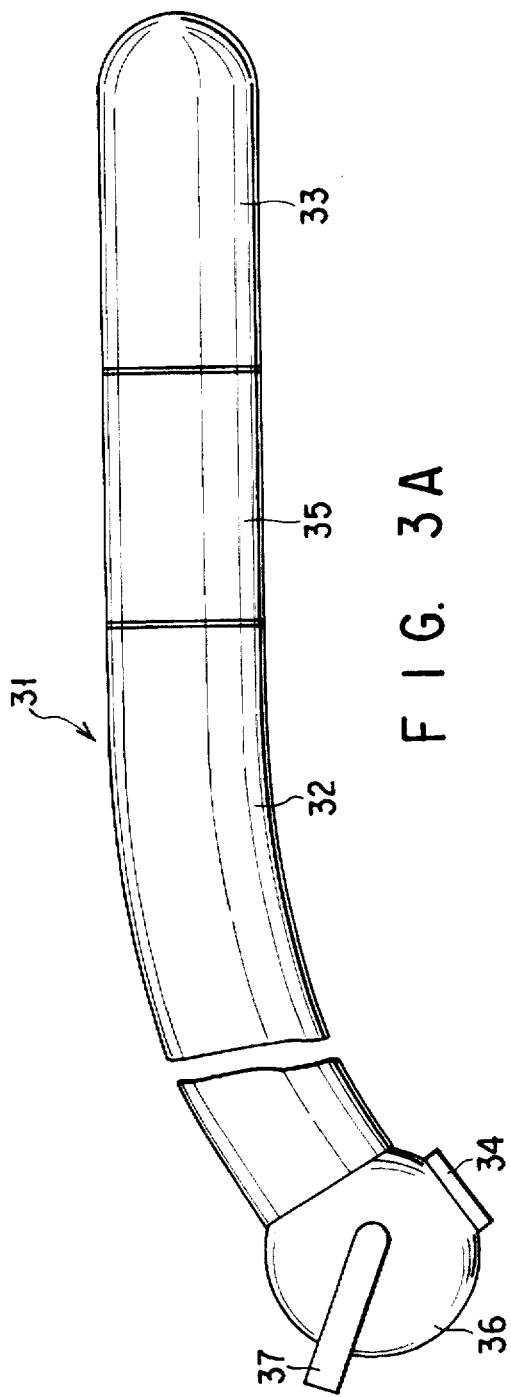
FIGS. 3A, 3B and 3C are views schematically showing the structure of a device according to seventh, eighth and ninth embodiments of the present invention.
Figure 3B:
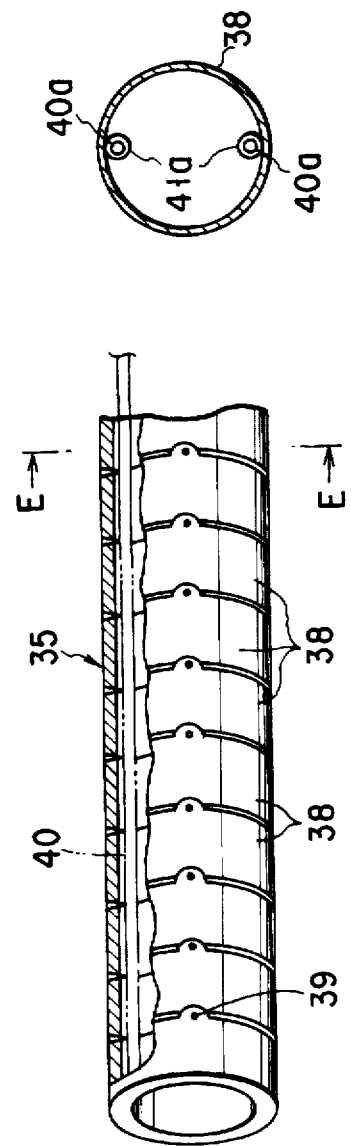
Figure 3C:

FIGS. 3A, 3B and 3C schematically show the structure of a device 31 for a magnetic resonance imaging apparatus according to the seventh embodiment of the present invention. In these figure, FIG. 3A shows the entire device, FIG. 3B shows an example of the frame structure of a bend portion which will be explained later, and FIG. 3C is a cross-section cut along a line E—E of FIG. 3B.

In this seventh embodiment, the device 31 which can be inserted into body cavities includes an insertion portion comprising of a flexible tube, a distal end portion 33, and a magnetic resonance signal output portion 34, like in the first embodiment, and further includes a bend portion 35 inserted between the insertion portion 32 and the distal end portion 33. A main body member 36 of the magnetic resonance signal output portion 34 is provided at a bottom end of the insertion portion 32. The main body member 36 is provided with an operating means for controlling the bending of the bend portion 35.

The frame of the bend portion 35 is arranged as shown in FIGS. 3B and 3C. This frame of the bend portion comprises a plurality of short tube-like frame pieces 38, junction portions 39 including pins for pivot-connecting adjacent frame pieces 38, wires 40a for rotating adjacent frame pieces 38 around the junction portions 39 as fulcrums, thereby to bend the entire bending portion 35, and wire receivers 41a through which the wires 40a penetrate. Two wires 40a are provided respectively at upper and lower positions, and therefore, two wire receivers are provided at upper and lower positions, too. In the insertion portion 32, the wires 40a are guided to an operating means 37 incorporated in the main body member 36 of the magnetic resonance signal output portion 34. However, the number of wires 40a is not limited to two. As an outer layer of the frame of the bend portion, a cylindrical net made of natural or artificial fibers may be used, and further, an upper coating member made of elastomer may be provided as an upper outer layer over the outer layer.

In this structure, the material forming the distal end portion 33 has a magnetic permeability lower than those of the materials forming the bend portion 35, the insertion portion 32, the operating means 37, and the magnetic resonance signal output portion 34. As a typical example of this, there may be a distal end portion 33 made of resins when iron having a high purity is included in the materials forming the insertion portion 32, the bend portion 35, the magnetic resonance signal output portion 34, and the operating portion 37.

In addition, the shapes are not limited to those specified above, as long as the requirements also specified above are satisfied. The shape of the receiver coil 24 is not limited to a loop-like shape. The material of the signal receiver coil 24 is not limited to copper, as long as it is a low magnetic permeability metal which is electrically conductive. In addition, an elastomer for an outer layer of the bend portion may be made of natural or synthesized high polymer.

According to the seventh embodiment having the above structure, the insertion portion 32 is firstly inserted into a body cavity while adjusting the bend portion 35 by means of the operation means 37, and the distal end portion 33 is precisely positioned at a target portion. Further, the operation of a bend system is performed in such a manner in which the wires 40a are pulled by the operating means 37 connected to the wires 40a, and the frame pieces 38 are thereby rotated by a small angle with the junction portions 39 of the frame pieces 38 as their fulcrums. Thus, the bend portion 35 is bent. After insertion of the portion 32, the operation of the seventh embodiment is the same as that of the first embodiment.

This embodiment attains an advantage in that the insertion portion can be inserted more easily into to a patient and the distal end portion 33 can be precisely positioned at a target portion.

If a structure of an endoscope is incorporated in this device, the device further has a structure as a flexible scope so that observation using the endoscope function can simultaneously be carried out. The material of the structure of the endoscope must naturally be considered as having the same magnetic susceptibility as stated above.

Eighth Embodiment

This eighth embodiment has a structure similar to the seventh embodiment shown in FIGS. 3A, 3B and 3C except for the following difference. Specifically, in the device 31 for a magnetic resonance imaging apparatus according to the eighth embodiment, the materials forming the distal end portion 33 and the bend portion 35 have magnetic permeabilities lower than those of the materials forming the operating portion 32 and the magnetic resonance signal output portion 34. Further, the material forming the insertion portion 32 has a magnetic permeability lower than those of the materials forming the operating means 37, the main body member 36 including said means, and the magnetic resonance signal output portion 34. As a typical example of this, the distal end portion 33, the bend portion 35, and the insertion portion 32 are made of resins, when iron having a high purity is included in the materials forming the insertion portion 32, the operating means 37, and the magnetic resonance signal output portion 38.

In addition, the shapes are not limited to those specified above, as long as the requirements also specified above are satisfied. The shape of the magnetic resonance signal receiver coil 24 is not limited to a loop-like shape. The material of the signal receiver coil is not limited to copper, as long as it is a low magnetic permeability metal which is electrically conductive.

The eighth embodiment having the above structure attains the same operation as the seventh embodiment. Therefore, according to this embodiment, the same advantages as obtained in the seventh embodiment can be attained. Further, according to this eighth fifth embodiment, not only the distal end portion 33 and the bend portion 35 but also the insertion portion 32 is not attracted by a magnet of a magnetic resonance video device, so that safety can be ensured for both of an operator and a patient.

Ninth Embodiment

This ninth embodiment has the same structure as the seventh embodiment shown in FIGS. 3A, 3b and 3C, except the following respect.

In the device 31 for a magnetic resonance imaging apparatus, the materials forming the distal end portion 33 has a magnetic permeability lower than those of the materials forming the insertion portion 32 and the magnetic resonance signal output portion 34, and the material forming the insertion 32 has a magnetic permeability lower than that of the material forming the magnetic resonance signal output portion 34.

Further, the materials forming the magnetic resonance signal output portion 34 and the operating means 37 have magnetic permeabilities equal to or lower than those of metallic materials forming a conventional endoscope operating portion.

In addition, the shapes are not limited to those specified above, as long as the requirements also specified above are satisfied. The shape of the signal receiver coil is not limited to a loop-like shape. The material of the signal receiver coil is not limited to copper, as long as it is a low magnetic permeability metal which is electrically conductive.

The ninth embodiment having the above structure performs the same operation as that of the seventh embodiment described above. According to this embodiment, an advantage is obtained in that the entire insertion portion 32 is not attracted by a magnet so that safety can always be ensured for both of an operator, an assistant operator, and a patient, in addition to the advantages obtained in the fifth embodiment.

Tenth Embodiment

FIGS. 4 schematically show the structure of a device 31 for a magnetic resonance imaging apparatus according to the tenth embodiment of the present invention. In this embodiment, the structures of the bend portion 35 and the distal end portion 33 are the same as those used in the fourth and seventh embodiments. In this embodiment, the device 31 comprises a distal end portion 33 having the same structure as in the fourth embodiment, an insertion portion 32 which is made of a hard tube and can be inserted into a body, a bend portion 35 having the same structure as in the seventh embodiment, a magnetic resonance signal output portion 34 for outputting a magnetic resonance signal received by the distal end portion 33 to the magnetic resonance imaging apparatus coupled with the device, and an operating means used to bend the device.

In this structure, the material forming the distal end portion 33 has a permeability lower than those of the materials forming the bend portion 35, the insertion portion 32, the magnetic resonance signal output portion 34, and the operating means 37.

As a typical example, the insertion portion 33 may be formed of resins when iron having a high purity is included in the materials forming the insertion portion 32, the bend portion 35, the magnetic resonance signal output portion 34, and the operating means 37.

In addition, the shapes are not limited to those specified above, as long as the requirements also specified above are satisfied. The shape of the receiver coil is not limited to a loop-like shape. The material of the coil is not limited to copper, as long as it is a low magnetic permeability metal which is electrically conductive.

According to the tenth embodiment having the above structure, the device is inserted into a body, particularly into a ventricle, a pleural cavity, a joint, or a peritoneal cavity, while bending it if necessary, and the distal end portion 33 is precisely positioned at a target portion. The operation of the bend portion is the same as that of the seventh embodiment. Also, the operation after insertion of the device is the same as the seventh embodiment.

According to the this embodiment, another advantage is obtained in that the device can be inserted into a body, particularly into a ventricle, a pleural cavity, a joint, or a peritoneal cavity while bending the device if necessary, and the distal end portion can be precisely positioned at a target portion, in addition to the advantages obtained in the first embodiment.

Eleventh Embodiment

This eleventh embodiment has a structure similar to the tenth embodiment shown in FIG. 4 except for the following difference. Specifically, in the device 31, the materials forming the distal end portion 33 and the bend portion 35 have magnetic permeabilities lower than those of the materials forming the insertion portion 32, the magnetic resonance signal output portion 34, and the operating means 37.

Further, the material forming the insertion portion 32 forming part of an intermediate member of the body of the device has a magnetic permeability lower than those of the materials forming the operating means 37 and the magnetic resonance signal output portion 34 which form part of a handling side portion of the body of the device. As a typical example of this, the distal end portion 33, the bend portion 35, and the insertion portion 32 are made of resins, when iron having a high purity is included in the materials forming the operating portion 37 and the magnetic resonance signal output portion 34.

In addition, the shapes are not limited to those specified above, as long as the requirements also specified above are satisfied. The shape of the receiver coil is not limited to a loop-like shape. The material of the receiver coil is not limited to copper, as long as it is a low magnetic permeability metal which is electrically conductive.

The eleventh embodiment having the above structure attains the same operation as the tenth embodiment explained above. Further, according to the this embodiment, another advantage is obtained in that not only the distal end portion 33 but also the bend portion 35 and the insertion portion 32 are not attracted by a magnet of a magnetic resonance imaging apparatus, so that safety can be ensured for both of an operator and a patient during use of the device 31, in addition to the same advantages as obtained in the tenth embodiment.

Twelfth Embodiment

This twelfth embodiment is based on the same structure as the tenth embodiment shown in FIG. 4, and is further characterized in the following respect. The materials forming the distal end portion 33 and the bend portion 35 have permeabilities lower than those of the materials forming the insertion portion 32, the operating means 37, and the magnetic resonance signal output portion 34. The material forming the insertion portion 32 has a permeability lower than the operating means 37 and the magnetic resonance signal output portion 34 in the handling side.

Further, the materials forming the operating means 37 and the magnetic resonance signal output portion 34 have magnetic permeabilities equal to or lower than those of metallic materials forming a conventional endoscope operating portion.

In addition, the shapes are not limited to those specified above, as long as the requirements also specified above are satisfied. The shape of the signal receiver coil is not limited to a loop-like shape. The material of the signal receiver coil is not limited to copper, as long as it is a low magnetic permeability metal which is electrically conductive.

The twelfth embodiment having the above structure operates in the same manner as in the tenth embodiment described above. According to this embodiment, another advantage is obtained in that the entire device is not attracted by a magnet so that safety can always be ensured for an operator, an assistant operator, and a patient, including the time when the device is used, in addition to the advantages obtained in the eleventh embodiment.

Thirteenth Embodiment

FIGS. 5A and 5B schematically show the structure of a device for a magnetic resonance imaging apparatus according to the thirteenth embodiment of the present invention. In these figures, FIG. 5A is a perspective view showing the entire device, and FIG. 5B shows an example of the frame structure of a bend portion.

In this embodiment, an insertion device 40 made of a tube comprises a distal end portion 41 having an opening for an optical system and a conduit system both not shown, a signal receiver coil container portion 42 having the same structure as the distal end portion of the first embodiment, and an insertion portion 43 which is made of a flexible tube and can be inserted into a body cavity. Further, a handling side portion 44 which is always kept outside the body is provided at a bottom end of the insertion portion 43. The handling side portion 44 includes a forceps opening 45, an eye-piece portion 47 having an eye-piece optical system 46, and a retaining portion 48 provided between the forceps opening 45 and the eye-piece portion 47. Further, the handling side portion 44 is connected with a universal cord 49 in which an illumination optical system and a magnetic resonance signal transmission system are inserted. An extended top end of the universal cord 49 is provided with a connector 50 for receiving illumination light from a light source not shown, and a magnetic resonance signal output portion 51 for outputting a magnetic resonance signal received by the container portion 42 to a magnetic resonance imaging apparatus coupled with the device but not shown in the figure.

As shown in FIG. 5B, a flexible tube constituting the insertion portion 43 comprises a bend member 54 which is made of metal or non-metal and has a spiral structure which allows a frame member to be flexible, a cylindrical net 55 made of metal or resins which covers the outer layer of the bend member, and a coating member 56 as an uppermost outer layer made of natural or synthetic resins.

In this structure, the material forming the container portion 42 has a permeability lower than those of the materials forming the distal end portion 41, the insertion portion 43, the forceps opening 45, the eye-piece optical system 46, the eye-piece portion 47, the retaining portion 48, the universal cord 49, the connector 50, and the magnetic resonance signal output portion 51. As a typical example thereof, the container portion 42 may be formed of resins when iron or the like having a high purity is included in the materials forming the portions other than the container portion 42. The distal end portion 41, however, may include a slight amount of low magnetic permeability metal.

In addition, the shapes are not limited to those specified above, as long as the requirements also specified above are satisfied. The shape of the receiver coil is not limited to a loop-like shape. The material of the coil is not limited to copper, as long as it is a low magnetic permeability metal which is electrically conductive.

According to the thirteenth embodiment having the above structure, a tube is inserted into a body cavity while observing the inside of the body cavity by means of an eye-piece optical system 46, and thus, the container portion 42 is precisely positioned at a target portion.

After insertion of the tube, a magnetic resonance signal received by a magnetic resonance signal receiver coil not shown but included in the container portion 42 is transmitted to a magnetic resonance cross-section video apparatus not shown through the insertion portion 43, the retaining portion 48, a signal transmit means not shown but included in the universal cord 49, and the magnetic resonance signal output portion 51 connected to the transmit means. The signal is supplied from the output portion 51 to a magnetic resonance video apparatus, and accordingly, an MR-image is obtained. This MR-image may be displayed on one single monitor screen together with an endoscope optical image.

Therefore, according to this embodiment, another advantage is obtained in that an endoscope image can be observed so that observation and a diagnosis can be performed using both of the MR- and endoscope images, in addition to the same advantages as obtained in the first embodiment.

Further, both of an MR-image and an endoscope image may be displayed on one single monitor, or these images may otherwise be displayed in a different manner.

Fourteenth Embodiment

A magnetic resonance imaging device 40 according to the fourteenth embodiment has a structure similar to the thirteenth embodiment shown in FIGS. 5A and 5B. In this fourteenth embodiment, the materials forming the container portion 42 and the distal end portion 41 have magnetic permeabilities lower than those of the materials forming the insertion portion 43, the forceps opening 45, the eye-piece optical system 46, the eye-piece portion 47, the retaining portion 48, the universal cord 49, the connector 50, and the magnetic resonance signal output portion 51. Further, the material forming the insertion portion 43 has a magnetic permeability lower than those of the materials forming the other portions than the container portion and the distal end portion 41. Specifically, the portions are divided into three regions whose magnetic permeabilities are different from each other. As a typical example of this, the insertion portion 43, the container portion 42, and the distal end portion 41 are made of resins, when iron having a high purity is included in the materials forming the other portions than the insertion portion 43, the container portion 42, and the distal end portion 41. The insertion portion 43, however, may include a small amount of low magnetic permeability metal.

In addition, the shapes are not limited to those specified above, as long as the requirements also specified above are satisfied. The optical system may use a pick-up element to perform electric treatments. The shape of the receiver coil is not limited to a loop-like shape. The material of the receiver coil is not limited to copper, as long as it is a low magnetic permeability metal which is electrically conductive.

The fourteenth embodiment having the above structure operates in the same manner as in the thirteenth embodiment explained above. Further, according to the this embodiment, another advantage is obtained in that not only the distal end portion 41 and the container portion 42 but also the insertion portion 43 is not attracted by a magnet of a magnetic resonance video apparatus, so that safety can be ensured for both of an operator and a patient during use of the device, in addition to the same advantages as obtained in the thirteenth embodiment.

Fifteenth Embodiment

This fifteenth embodiment has a structure similar to the thirteenth embodiment shown in FIGS. 5A and 5B. In a device 40 for a magnetic resonance imaging apparatus, the materials forming the distal end portion 41 and the container portion 42 have magnetic permeabilities lower than those of the distal end portion 41, the insertion portion 43, the forceps opening 45, the eyepiece optical system 46, the eye-piece portion 47, the retaining portion 48, the universal cord 49, the connector 50, and the magnetic resonance signal output portion 51. In addition, the material forming the insertion portion 43 has a magnetic permeability lower than those of the materials forming the other portions than the distal end portion 41 and the container portion 42.

Further, the materials forming the portions other than the distal end portion 41, including the container portion 42, and the insertion portion 43 have magnetic permeabilities equal to or lower than metal materials forming an operating portion of a conventional endoscope.

In addition, the shapes are not limited to those specified above, as long as the requirements also specified above are satisfied. The optical system may use a pick-up element to perform electric treatments. The material of the signal receiver coil is not limited to copper, as long as it is a low magnetic permeability metal which is electrically conductive.

The fifteenth embodiment having the above structure operates in the same manner as in the thirteenth embodiment described above. Further, according to this embodiment, another advantage is obtained in that the entire tube of the device is not attracted by a magnet so that safety can always be ensured for an operator, an assistant operator, and a patient, including the operating time in which the device is used, in addition to the advantages obtained in the fourteenth embodiment.

Sixteenth Embodiment

FIG. 6 shows an outer appearance of the sixteenth embodiment of the present invention. A tube of the device 60 for a magnetic resonance imaging apparatus according to this sixteenth embodiment comprises a distal end portion 61 having an optical system not shown, a coil container portion 62 having the same structure as the fourth embodiment explained above, and a hard insertion portion 63 having the same structure as the fourth embodiment. An eye-piece portion 65 having an eye-piece optical system 64 as well as a retaining portion 66 are provided at a bottom end of the insertion portion 63. Further, the retaining portion 66 is connected with a universal cord 67 in which an illumination optical system and a magnetic resonance signal transmission system are inserted. An extended top end of the universal cord 67 is provided with a connector 68 for receiving illumination light from a light source not shown, and a magnetic resonance signal output portion 69 for outputting a magnetic resonance signal received by the container portion 62 to a magnetic imaging apparatus coupled with the device but not shown in the figure.

In this structure, the material forming the container portion 62 has a permeability lower than those of the materials forming the distal end portion 61, the insertion portion 63, the eye-piece optical system 64, the eye-piece portion 65, the retaining portion 66, the universal cord 67, the connector 68, and the magnetic resonance signal output portion 69.

As a typical example thereof, the container portion 62 may be formed of resins when iron or the like having a high purity is included in the materials forming the portions other than the container portion 62.

In addition, the shapes are not limited to those specified above, as long as the requirements also specified above are satisfied. The optical system may uses a pick-up element to perform electric treatments. The shape of the receiver coil is not limited to a loop-like shape. The material of the coil is not limited to copper, as long as it is a low magnetic permeability metal which is electrically conductive.

According to the sixteenth embodiment having the above structure, a tube is inserted into a body, particularly into a ventricle, a pleural cavity, a joint, or a peritoneal cavity, while observing the inside of the body by means of the eye-piece optical system 64, and the container portion is precisely positioned at a target portion when a tube is thus inserted into a body, a hard tube such as a a tracheal tube not shown which can be inserted into the body from outside may be subsidiarily used.

After insertion of the tube, a magnetic resonance signal received by a magnetic resonance signal receiver coil not shown but included in the container portion 62 is transmitted to a magnetic resonance imaging apparatus not shown through the insertion portion 63, the retaining portion 66, a signal transmit means not shown but included in the universal cord 67, and the magnetic resonance signal output portion connected to the transmit means. The signal is supplied from the output portion to a magnetic resonance video apparatus, and accordingly, an MR-image is obtained. This MR-image may be displayed on one single screen together with an endoscope optical image.

According to this embodiment, another advantage is obtained in that a tube can be easily inserted into a body, particularly into a ventricle, a pleural cavity, a joint, or a peritoneal cavity, and the receiver coil container portion can be precisely positioned at a target portion, in addition to the advantages obtained in the fourth embodiment. Further, an endoscope image can be observed so that observation and a diagnosis can be performed using both of the MR- and endoscope images.

Further, both of an MR-image and an endoscope image may be displayed on one single monitor, or these images may otherwise be displayed in a different manner.

Seventeenth Embodiment

The seventeenth embodiment has a structure similar to the sixteenth embodiment shown in FIG. 6. In a tube used in the device of this embodiment, however, the materials forming the distal end portion 61 and the container portion 62 have magnetic permeabilities lower than those of the materials forming the insertion portion 63, the eye-piece optical system 64, the eye-piece portion 65, the retaining portion 66, the universal cord 67, the connector 68, and the magnetic resonance signal output portion 69.

Further, the material forming the insertion portion 63 has a magnetic permeability lower than those of the materials forming the other portions including the container portion 62 and the distal end portion 61. As a typical example of this, the insertion portion 63, the container portion 62, and the distal end portion 61 are made of resins, when iron having a high purity is included in the materials forming the other portions than the insertion portion 63, the container portion 62, and the distal end portion 61. The insertion portion 63, however, may include a small amount of low magnetic permeability metal.

In addition, the shapes are not limited to those specified above, as long as the requirements also specified above are satisfied. The optical system may use a pick-up element to perform electric treatments. The shape of the receiver coil is not limited to a loop-like shape. The material of the receiver coil is not limited to copper, as long as it is a low magnetic permeability metal which is electrically conductive.

The seventeenth embodiment having the above structure operates in the same manner as in the sixteenth embodiment explained above. Therefore, according to the this embodiment, another advantage is obtained in that not only the distal end portion 61 and the container portion 62 but also the insertion portion 63 is not attracted by a magnet of a magnetic resonance video apparatus, so that safety can be ensured for both of an operator and a patient during use of the device, in addition to the same advantages as obtained in the sixteenth embodiment.

Eighteenth Embodiment

The eighteenth embodiment has a structure similar to the sixteenth embodiment shown in FIG. 6. In a tube of the eighteenth embodiment according to the present invention, however, the materials forming the distal end portion 61 and the container portion 62 have magnetic permeabilities lower than those of the materials forming the insertion portion 63, the eye-piece optical system 64, the eye-piece portion 65, the retaining portion 66, the universal cord 67, the connector 68, and the magnetic resonance signal output portion 69. The material forming the insertion portion 63 has a magnetic permeability lower than those of the materials forming the portions other than the container portion 62 and the distal end portion 61.

Further, the materials forming the other portions than the insertion portion 63, the container portion 62, and the distal end portion 61 have permeabilities equal to or lower than that of metal material forming an operating portion of a conventional endoscope.

In addition, the shapes are hot limited to those specified above, as long as the requirements also specified above are satisfied. The optical system may use a pick-up element to perform-electric treatments. The shape of the receiver coil is not limited to a loop-like shape. The material of the receiver coil is not limited to copper, as long as it is a low magnetic permeability metal which is electrically conductive.

The eighteenth embodiment having the above structure operates in the same manner as in the sixteenth embodiment explained above. However, according to the this embodiment, another advantage is obtained in that the entire tube of the device is not attracted by a magnet, so that safety can always be ensured for an operator, an assistant operator, and a patient, including the time while the device is used, in addition to the same advantages as obtained in the seventeenth embodiment.

Nineteenth Embodiment

Figures 7A, 7B:
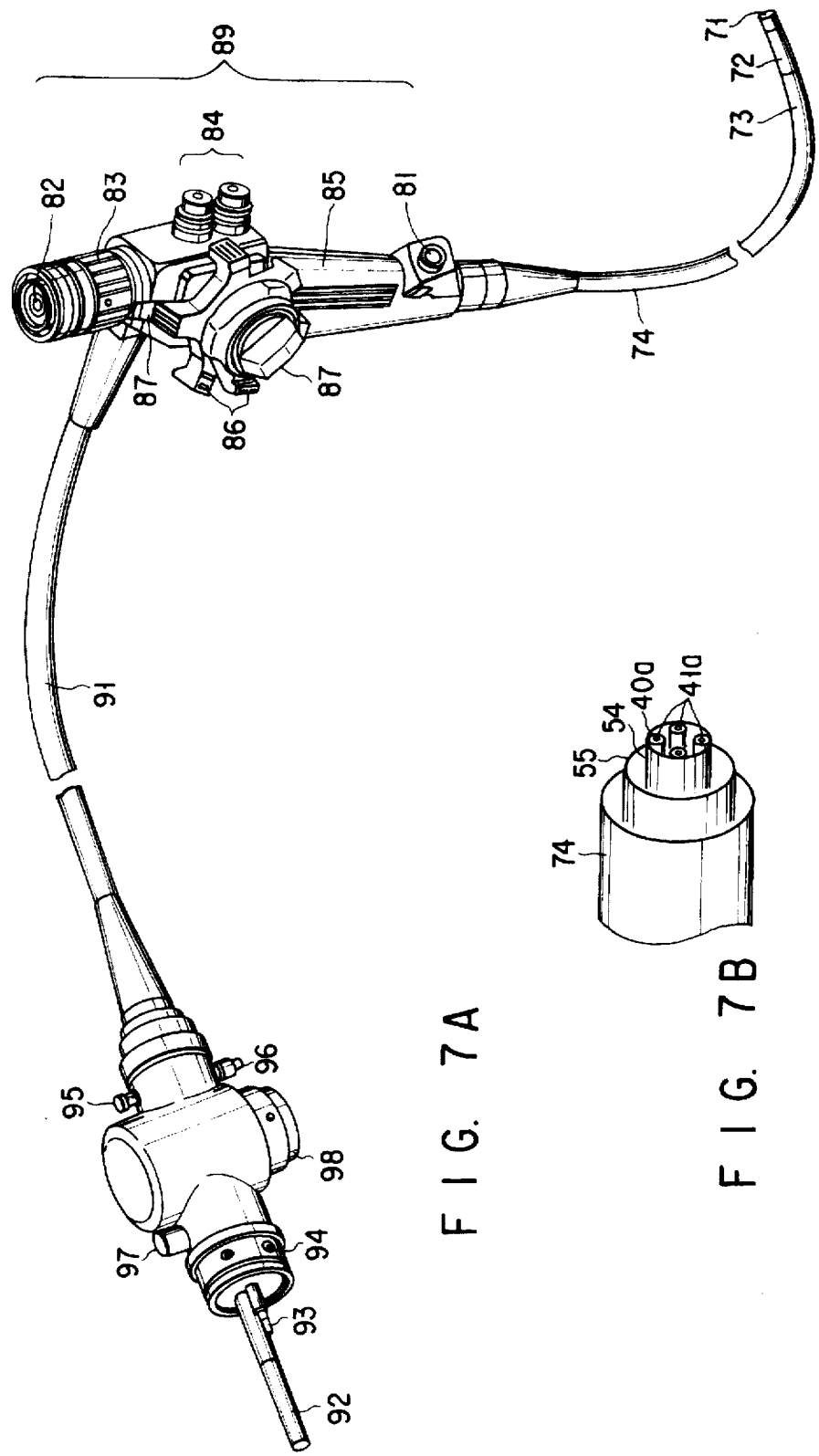
FIGS. 7A and 7B are views schematically showing the structure of a device according to nineteenth to twenty-first embodiments of the present invention.

FIGS. 7A and 7B schematically show the structure of a device for a magnetic resonance imaging apparatus according to the nineteenth embodiment of the present invention. In this embodiment, a tube of the device comprises a distal end portion 71 having an opening for an optical system and a conduit system both not shown, a magnetic resonance signal receiver coil container portion 72 having the same structure as the in the first embodiment, a bend portion 73 having the same structure as in the seventh embodiment, an insertion portion 74 provided with wires 40a for bending the device and with guide members 41a for protecting the wires 40a in a flexible tube having the same structure as in the thirteenth embodiment, a forceps opening 81, an eye-piece portion 83 having an eye-piece optical system 82, a conduit system control means 84 for controlling the conduit system, a retaining portion 85, a bending control means 86 for controlling bending of the device, and a bending maintain means 87 for maintaining an arbitrary bending state.

An operating portion 89 of the device is constituted by the forceps opening 81, the eye-piece optical system 82, the eye-piece portion 83, the conduit system control means 84, the retaining portion 85, the bending control means 86, and the bending maintain means 87. This operating portion is provided with a universal cord 91 in which an illumination optical system and a magnetic resonance signal transmission system are inserted, a connector 92 for receiving illumination light from a light source not shown, an air-feed hole 93 for receiving air from a light source device not shown, electric contact points 94 for supplying the eye-piece portion 83 with an electric power source, a connector receiver 95 for releasing a high-frequency leakage current, an intake hole 96, a water feed hole 97, and a magnetic resonance signal output portion 98 for outputting a magnetic resonance signal received by the container portion 72 to a magnetic resonance imaging apparatus coupled with the device. The device according to this embodiment is constituted by the components as cited above.

In this structure, the material forming the container portion 72 has a permeability lower than those of the materials forming the portions other than the container portion. As a typical example thereof, the container portion 72 may be formed of resins when iron or the like having a high purity is included in the materials forming the portions other than the container portion 72.

In addition, the shapes are not limited to those specified above, as long as the requirements also specified above are satisfied. The shape of the receiver coil is not limited to a loop-like shape. The material of the coil is not limited to copper, as long as it is a low magnetic permeability metal which is electrically conductive.

According to the nineteenth embodiment having the above structure, a tube is inserted into a body cavity while observing the inside of the body cavity by means of an eye-piece optical system and while adjusting the bend portion 73 by means of the bending control means 86 and the bending maintain means 87, and thus, the container portion 72 is precisely positioned at a target portion.

After insertion of the tube, a magnetic resonance signal received by a magnetic resonance signal receiver coil not shown but included in the container portion 42 is transmitted to a magnetic resonance video apparatus not shown through the insertion portion 74, the operating portion 89, a signal transmit means not shown but included in the universal cord 91, and the magnetic resonance signal output portion 98 connected to the transmit means. Accordingly, an MR-image is obtained. This MR-image may be displayed on one single monitor screen together with an endoscope optical image.

According to this embodiment, another advantage is obtained in that a tube can be more easily inserted into a body cavity with much less burdens to a patient, and the receiver coil container portion can be precisely positioned at a target portion.

Twentieth Embodiment

A device for a magnetic resonance imaging apparatus according to this twentieth embodiment has the same structure as the nineteenth embodiment shown in FIGS. 7A and 7B. In a tube of the device of the twentieth embodiment, however, the materials forming the distal end portion 71, the container portion 72, and the bend portion 73 have magnetic permeabilities lower than those of the materials forming the portions other than these portions 71, 72, and 73.

Further, the material forming the insertion portion 74 has a magnetic permeability lower than those of the materials forming the portions other than the distal end portion 71, the container portion 72, and the bend portion 73. As a typical example thereof, the insertion portion 74, the bend portion 73, the container portion 72, and the distal end portion 71 may be formed of resins when iron or the like having a high purity is included in the materials forming the portions other than the insertion portion 74, the bend portion 73, the container portion 72, and the distal end portion 71. The insertion portion 74 may include a small amount of low magnetic permeability metal.

In addition, the shapes are not limited to those specified above, as long as the requirements also specified above are satisfied. The shape of the signal receiver coil is not limited to a loop-like shape. The material of the signal receiver coil is not limited to copper, as long as it is a low magnetic permeability metal which is electrically conductive.

The twentieth embodiment having the above structure operates in the same manner as in the nineteenth embodiment described above. According to this embodiment, an advantage is obtained in that not only the distal end portion 71, the container portion 72, and the bend portion 73 but also the insertion portion 74 is not attracted by a magnet of a magnetic resonance video apparatus, so that safety can be ensured for both of an operator and a patient, in addition to the advantages obtained in the nineteenth embodiment.

Twenty-first Embodiment

The twenty-first embodiment has the same structure as the nineteenth embodiment shown in FIGS. 7A and 7B. In this embodiment, the materials forming the distal end portion 71, the container portion 72, and the bend portion 73 have magnetic permeabilities lower than those of the materials forming the other portions than these portions 71, 72, and 73, and the material forming the insertion portion 74 has a magnetic permeability lower than those of the materials forming the portions other than the distal end portion 71, the container portion 72, and the bend portion 73 (this corresponds to claim 1).

Further, the materials forming the portions other than the distal end portion 71, the container portion 72, the bend portion 73, and the insertion portion 74 have permeabilities equal to or lower than that of metal material forming an operating portion of a conventional endoscope.

In addition, the shapes are not limited to those specified above, as long as the requirements also specified above are satisfied. The optical system may use a pick-up element to perform electric treatments. The shape of the signal receiver coil is not limited to a loop-like shape. The material of the signal receiver coil is not limited to copper, as long as it is a low magnetic permeability metal which is electrically conductive.

The twenty-first embodiment having the above structure operates in the same manner as in the twentieth embodiment described above. According to this embodiment, an advantage is obtained in that the entire tube of the device is not attracted by a magnet resonance video apparatus of a magnetic so that safety can be ensured for an operator, an assistant operator, and a patient, including the time when the device is used, in addition to the same advantages as obtained in the twentieth embodiment.

Twenty-second Embodiment

FIGS. 8A and 8B schematically show the structure of a device according to the twenty-second embodiment of the present invention, wherein FIG. 8A shows a perspective view of the entire outer appearance of the device, and FIG. 8B is a perspective view showing a partial cross-section of an insertion portion which will be described later.

In this embodiment, a tube of the device comprises a distal end portion 71 having an opening for an optical system and a conduit system both not shown, a receiver coil container portion 72 having the same structure as in the fourth embodiment, a bend portion 73 having the same structure as in the seventh embodiment, wires 40a for bending the device as shown in FIG. 8B, protection guide members 41a for receiving and guiding the wires 40a, an insertion portion 74 including of a hard tube which can be inserted into a body, an insertion hole 101, an eye-piece portion 103 having an eye-piece optical system 102, a retaining portion 104, a bending control means 105 for controlling bending of the device, and a bending maintain means 106 for maintaining an arbitrary bending state. An operating portion 107 is constituted by the insertion hole 101, the eye-piece portion 103, the retaining portion 104, the bending control means 105, and the bending maintain means 106. Further, this device comprises a universal cord 111 in which an illumination optical system and a magnetic resonance signal transmission system are inserted, and the universal cord 111 has an extended top end provided with a connector 112 for receiving illumination light from a light source not shown, and a magnetic resonance signal output portion 113 for outputting a magnetic resonance signal received by the container portion 72 to a magnetic resonance imaging apparatus coupled with the device.

In this structure, the material forming the container portion 72 has a permeability lower than those of the materials forming the portions other than the container portion. As a typical example thereof, the container portion 72 may be formed of resins when iron or the like having a high purity is included in the materials forming the portions other than the container portion 72.

In addition, the shapes are not limited to those specified above, as long as the requirements also specified above are satisfied. The optical system may use a pick-up element to perform electric treatments. The shape of the receiver coil is not limited to a loop-like shape. The material of the coil is not limited to copper, as long as it is a low magnetic permeability metal which is electrically conductive.

According to the twenty-second embodiment having the above structure, the tube of the device is inserted into a body while observing the inside of the body by means of an eye-piece optical system and while adjusting the bend portion 73 by means of the bending control means 105 and the bending maintain means 106, and thus, the container portion 72 is precisely positioned at a target portion. When the device is inserted into a body, it is possible to subsidiarily use a hard tube not shown, in which the distal end portion 71, the container portion 72, and the insertion portion 74 can be inserted and which can be inserted into the body-from the outside thereof.

After insertion of the tube, a magnetic resonance signal received by a magnetic resonance signal receiver coil not shown but included in the container portion 72 is transmitted to a magnetic resonance video apparatus not shown through the insertion portion 74, the operating portion 107, a signal transmit means not shown but included in the universal cord 111, and the magnetic resonance signal output portion 113 connected to the transmit means. Accordingly, an MR-image is obtained. This MR-image may be displayed on one single monitor screen together with an endoscope optical image.

According to this embodiment, another advantage is obtained in that a tube of the device can be more easily inserted into a body, particularly into a ventricle, a pleural cavity, or a joint and the receiver coil container portion 72 can be precisely positioned at a target portion, in addition to the same advantages as obtained in the sixteenth embodiment.

Twenty-third Embodiment

The twenty-third embodiment has the same structure as the twenty-second embodiment shown in FIG. 8. In a tube of the device of this embodiment, particularly, the materials forming the distal end portion 71, the container portion 72, and the bend portion 73 have magnetic permeabilities lower than those of the materials forming the portions other than these portions 71, 72, and 73.

Further, the material forming the insertion portion 74 has a magnetic permeability lower than those of the materials forming the portions other than the distal end portion 71, the container portion 72, and the bend portion 73. As a typical example thereof, the insertion portion 74, the bend portion 73, the container portion 72, and the distal end portion 71 may be formed of resins when iron or like materials having a high purity is included in the materials forming the portions other than the insertion portion 74, the bend portion 73, the container portion 72, and the distal end portion 71. The insertion portion 74 may include a small amount of low magnetic permeability metal.

In addition, the shapes are not limited to those specified above, as long as the requirements also specified above are satisfied. The optical system may use a pick-up element to perform electric treatments. The shape of the signal receiver coil is not limited to a loop-like shape. The material of the signal receiver coil is not limited to copper, as long as it is a low magnetic permeability metal which is electrically conductive.

The twenty-third embodiment having the above structure operates in the same manner as in the twenty-second embodiment described above. According to this embodiment, another advantage is obtained in that not only the distal end portion 71, the container portion 72, and the bend portion 73 but also the insertion portion 74 is not attracted by a magnet of a magnetic resonance imaging apparatus, so that safety can be ensured for both of an operator and a patient during use of the device, in addition to the advantages obtained in the twenty-second embodiment.

Twenty-fourth Embodiment

The twenty-fourth embodiment has the same structure as the twenty-second embodiment shown in FIGS. 8A and 8B. In this embodiment, particularly, the materials forming the distal end portion 71, the container portion 72, and the bend portion 73 of the device have magnetic permeabilities lower than those of the materials forming the portions other than these portions 71, 72, and 73, and the material forming the insertion portion 74 has a magnetic permeability lower than those of the materials forming the portions other than the distal end portion 71, the container portion 72, and the bend portion 73.

Further, the materials forming the portions other than the distal end portion 71, the container portion 72, the bend portion 73, and the insertion portion 74 have permeabilities equal to or lower than that of metal material forming an operating portion of a conventional endoscope.

In addition, the shapes are not limited to those specified above, as long as the requirements also specified above are satisfied. The optical system may use a pick-up element to perform electric treatments. The shape of the signal receiver coil is not limited to a loop-like shape. The material of the signal receiver coil is not limited to copper, as long as it is a low magnetic permeability metal which is electrically conductive.

The twenty-fourth embodiment having the above structure operates in the same manner as in the twentieth embodiment described above. According to this embodiment, another advantage is obtained in that the entire tube of the device is not attracted by a magnet so that safety can always be ensured for an operator, an assistant operator, and a patient, including the time when the device is used, in addition to the same advantages as obtained in the twenty-third embodiment.

Although the magnetic resonance signal receiver coil portion has been explained in the above embodiments, this coil portion may also be used to generate a resonance signal. Otherwise, another coil for generating a resonance signal may be provided in a probe.

In the embodiments of the present invention as has been stated above, an endoscope is cited as the device for a magnetic imaging apparatus. However, the features of the device according to the present invention are not limited to application to an endoscope, but can be applied to various operation treatment devices which are inserted into a body or a body cavity in a similar manner.

For example, the present invention can be applied to such an operation treatment device as will be exemplified by scissors-type forceps including a cutter means such as forceps at its distal end portion, an insertion portion, and a handling side operating portion, or by clamping forceps which has a similar structure except that a clamping means is provided at the distal end portion.

Otherwise, the present invention may be applied to a detection device as well be exemplified by a suction needle which has a tube path internally extending from a distal end portion through an insertion portion to a handling side portion and which sucks and collects organism tissue.

The following twenty-fifth to thirtieth embodiments relate to devices used for surgical operation under use of an endoscope. In recent years, surgical operations under use of an endoscope have been carried out mainly with use of a rigid scope such as a peritoneal cavity scope or the like and forceps. These devices have been applied not only to peritoneal cavities but also to brains, medullas, secondary nasal cavities and the like, which are difficult to view with eyes. In addition to such rigid scope, a soft scope is used depending on positions and usages. If these operations are carried out with use of a magnetic resonance imaging apparatus and an endoscope image and an MR-image are observed together, treatments can be made with much higher safety.

These operation devices need not always include a receiver antenna, but must be made of materials which do not influence MR-images. However, the entire device need not be made of such materials. More specifically, those portions of the device which are brought into contact with tissue and are positioned in the vicinity of a target portion to he treated must be made of material which do not cause disturbances in MR-images, i.e., materials having a extremely small magnetic susceptibility. On the other hand, those portions of the device which are inserted into a body and are positioned outside an area to be picked-up as an MR-image or positioned within a gas (which is not visualized in an MR-image) in a peritoneal cavity may be made of materials under less restricted conditions, and do not cause practical problems. Those portions of the device which are positioned outside a body are, apparently, not within the area picked up as an MR-image, and therefore, these portions may be made of materials which have a magnetic susceptibility higher than the other portions, as long as these portions are not attracted by a magnet.

Twenty-fifth Embodiment

Figure 9:
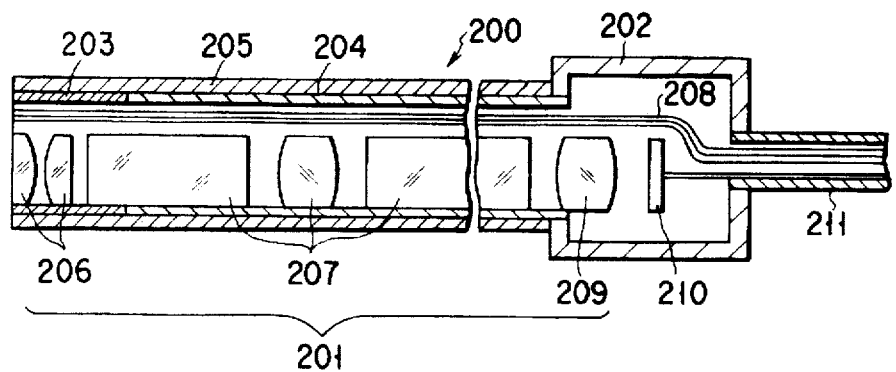
FIG. 9 is a view schematically showing the structure of a device according to a twenty-fifth embodiment of the present invention.

The device of this embodiment relates to a rigid scope 200 shown in FIG. 9, and this rigid scope 200 includes an insertion portion 201 and a retaining portion 202. The insertion portion 201 consists of a top end member 203 and an intermediate member 204, and a coating or a tube made of PTFE of a fluorine-based resin, ceramics or the like is coated so as to surround the insertion portion.

An objective lens system 206, a relay lens system 207, and a light guide cable 208 are provided in the insertion portion 201. The objective lens system 209 and a pick-up element 210 such as a solid-state pick-up element are arranged in the retaining portion 202, and the light guide cable 208 and a cable 211 including a cord of the pick-up element 210 are arranged at a rear end of the retaining portion 202.

Further, the magnetic susceptibility of the material forming the top end member 203 is greater than that of the material forming the intermediate member 204, which is greater than the material forming the retaining portion 202. For example, the top end member 203 is made of copper or aluminum, the intermediate member 204 is made of titanium or chatcopyrite, and the retaining portion 202 is made of austenite-based stainless steel or the like.

In general, when an operation is made with use of a laparoscope, the top end member 203 is positioned in the vicinity of a portion to be treated, the intermediate member 204 is positioned in an area of the peritoneal cavity which does not influence an MR-image, and the retaining portion 202 is positioned outside the body. Therefore, the structure as stated above does not influence MR-images. Further, there is a case where the rigid scope 200 is substantially inserted into tissue of an organism. In this case, it is desirable that the intermediate member 204 is made of the same material as that forming the top end member 203.

In this embodiment, since the pick-up element 210 is provided in the retaining portion 202, influences of noise onto an MR-image is reduced and a countermeasure for shielding can be easily provided in comparison with a structure in which a pick-up element is provided at a distal end portion.

In place of the relay lens system, a refractive index gradient type lens or an image conduit made of hardened glass fibers may be used.

Twenty-sixth Embodiment

Figure 10:
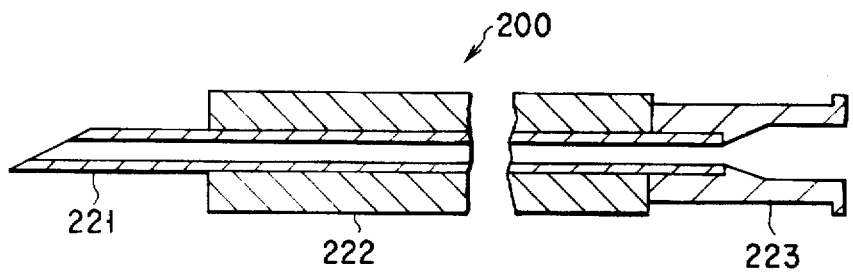
FIG. 10 is a view schematically showing the structure of an injection needle according to a twenty-sixth embodiment of the present invention.

The device of this embodiment relates to an injection needle 220 shown in FIG. 10. In this injection needle 220, the magnetic susceptibility of the material forming a needle 221 is greater than that of the material forming an insertion portion 222, which is greater than the material forming a connector 223.

Twenty-seventh Embodiment

Figure 11:
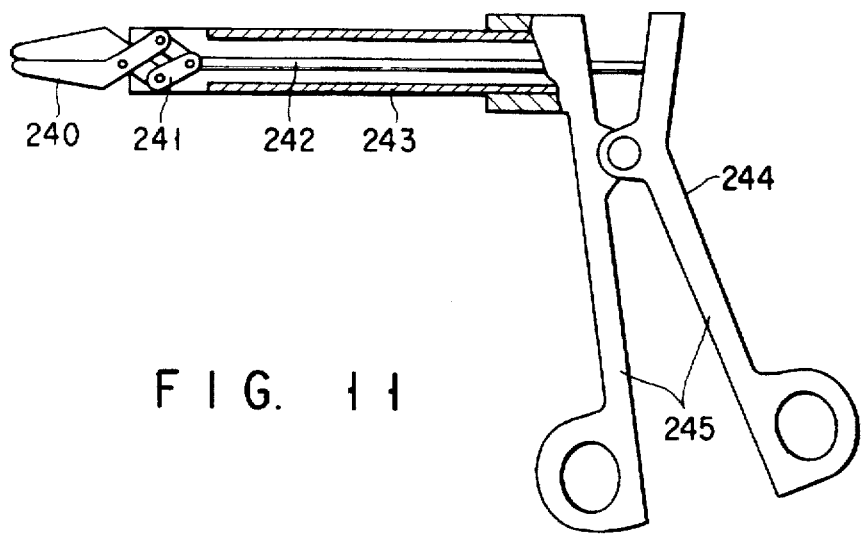
FIG. 11 is a view schematically showing the structure of forceps according to a twenty-seventh embodiment of the present invention.

The device of this embodiment relates to forceps shown in FIG. 11, and the material forming a jaw member 240 of the forceps has the smallest magnetic susceptibility. Materials forming a link member 241, a rod member 242, and a pipe member 243 have magnetic susceptibilities greater than that of the jaw member 240.

A member 245 of a handle portion 244 is made of a material having a magnetic susceptibility much greater than the materials of the members 241, 242, and 243. For example, the jaw member 241 is made of copper alloy coated with ceramics, titanium, or titanium alloy. The members other than the handle portion 244 may be formed of the material which has the smallest magnetic susceptibility. In this case, it is possible to obtain the same advantages as obtained in the twenty-sixth embodiment.

Twenty-eighth Embodiment

Figure 12:
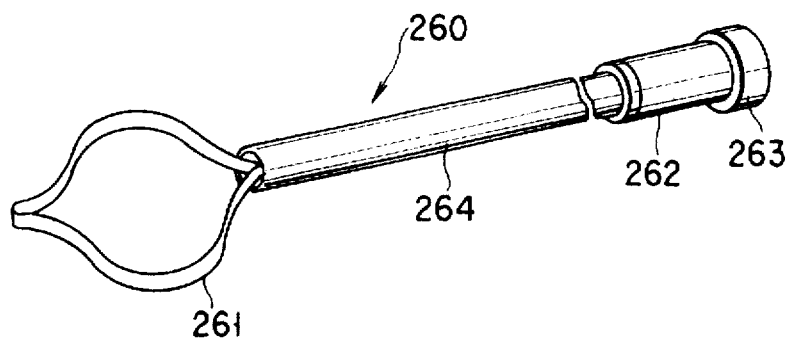
FIG. 12 is a view schematically showing the structure of a pressure emission element according to a twenty-eighth embodiment of the present invention.

The device of this embodiment relates to a pressure emission element 260 shown in FIG. 12. This pressure emission element has a top end member 261 formed into a loop-like shape, and the top end member 261 projects from and returns into the top end of an insertion portion 264 as a knobs 263 is moved forwardly and backwardly in relation to a handle 262. The top end member 261 is prepared by coating a strip made of copper or titanium with PTFE or the like, and this member has the smallest magnetic permeability among components constituting the pressure emission element 260.

Twenty-ninth Embodiment

Figure 13:
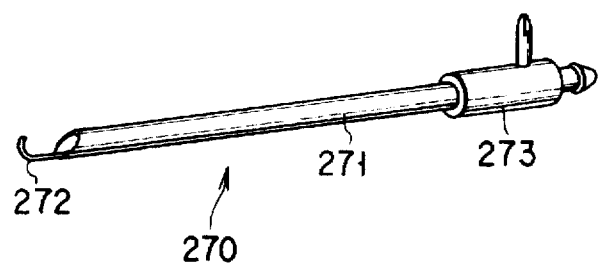
FIG. 13 is a view schematically showing the structure of a treatment electrode according to a twenty-ninth embodiment of the present invention.

The device of this embodiment relates to a treatment electrode 270 shown in FIG. 13. The electrode 270 is made of a material having a low magnetic susceptibility such as copper coated with titanium nitride (TIN), an insertion portion 271 is made of a material having a magnetic susceptibility greater than the material forming an electrode portion 272, such as stainless steel, chalcopyrite, titanium, or the like, and coated with an insulating coating made of PTFE or the like. A retaining portion 273 is made of a plastic material in view of electric safety.

Thirtieth Embodiment

Figure 15:
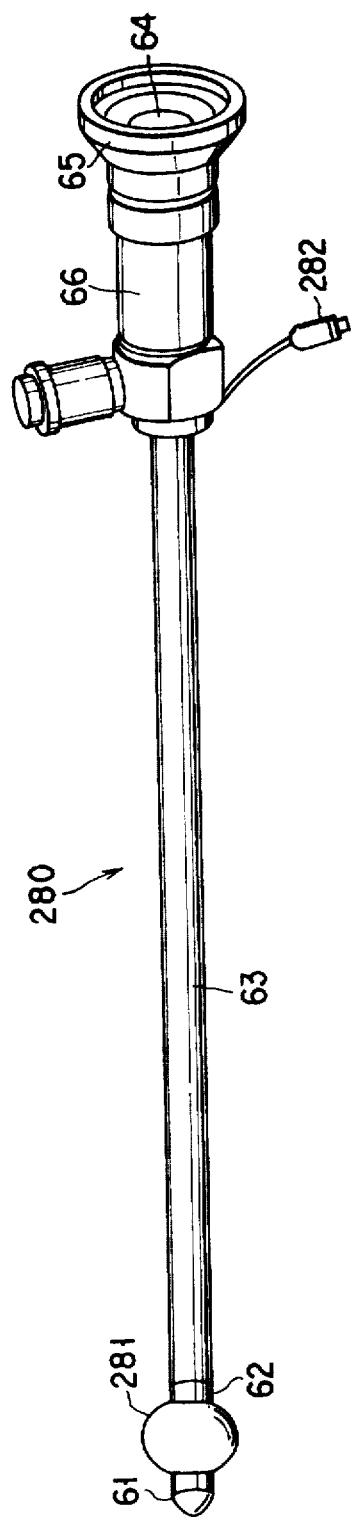
FIG. 15 is a view schematically showing the structure of a rigid scope according to a thirtieth embodiment of the present invention.

The device of this embodiment relates to a rigid scope 280 shown in FIG. 15, and this rigid scope 280 has a tissue pressure emission member, e.g., a balloon 281 which is expanded by feeding a gas through a mouth ring 282. This device has the same structure as shown in FIG. 6, except that a receiver antenna is not provided.

Since a space can be formed between the device and organism tissue by an expansion member 281, an MR-image of desired tissue is not influenced even when a material which slightly causes influences onto an MR-image is used in portions close to the top end of the device. This embodiment can be applied to a soft scope.

Thirty-first Embodiment

Figure 14:
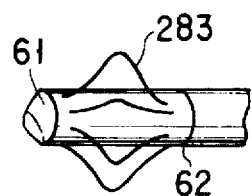
FIG. 14 is a view schematically showing the structure of a rigid scope according to a thirty-first embodiment of the present invention.

The device of this embodiment is a modification of the thirty embodiment. As shown in FIG. 14, a plurality of copper lines 283 coated with RTFE or the like are provided as a tissue pressure member, such that the copper lines can be expanded.

Although the magnetic resonance signal receiver coil portion may also be used to generate a resonance signal. Otherwise, another coil for generating a resonance signal may be provided in the device.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A device for use in combination with a magnetic resonance imaging apparatus which generates a static magnetic field and detects magnetic resonance in a living body placed in the static magnetic field, said device comprising:

a first distal end portion enterable into a region to be imaged by the apparatus and having at least one of a magnetic susceptibility and a magnetic permeability which has a value such that a uniformity of the static magnetic field generated by the apparatus remains substantially undistorted as the first portion is moved in a desired manner in the static magnetic field;

the first distal end portion including an antenna housing portion and a magnetic resonance signal-receiving antenna, the antenna housing portion having a portion which houses the magnetic resonance signal-receiving antenna, and the first distal end portion being formed of a material having a dielectric constant which decreases an attenuation of an electromagnetic wave having a magnetic resonance frequency; and a second proximal end portion unable to enter a body cavity and having at least one of a magnetic susceptibility and a magnetic permeability which is higher in a value thereof than a magnetic susceptibility and magnetic permeability of the first distal end portion and has a value such that the second proximal portion is not attracted to the static magnetic field; and a third intermediate portion unable to enter the region to be imaged, able to enter the body cavity, and having at least one of a magnetic susceptibility and a magnetic permeability which has a value higher than the value of the first distal end portion and lower than the value of the second proximal end portion and has at least one of the magnetic susceptibility and magnetic permeability such that disturbances in a uniformity of the static magnetic field are small, the third intermediate portion being connected at one end with said first distal end portion and connected at an opposite end with said second proximal end portion so as to be intermediate said first distal end portion and said second proximal end portion.

2. The device according to claim 1, further comprising an endoscope having a distal end section which comprises said first distal end portion.

3. The device according to claim 2, wherein said endoscope is a flexible scope.

4. The device according to claim 2, wherein said endoscope is a rigidoscope.

5. The device according to claim 1, further comprising a medical instrument which has an insertion section having a distal end portion which comprises said first distal end portion.

6. The device according to claim 1, further comprising a detection element having an insertion portion which comprises said first distal end portion.

7. The device according to claim 1, further comprising a coil provided in said first distal end portion, for receiving magnetic resonance signals.

8. The device according to claim 1, further comprising a coil provided in said first distal end portion, for causing magnetic resonance.

* * * * *